US009237913B2

(12) United States Patent
Gillard et al.

(10) Patent No.: US 9,237,913 B2
(45) Date of Patent: Jan. 19, 2016

(54) CERCLAGE SYSTEM FOR BONE

(71) Applicant: ACUTE Innovations, LLC, Hillsboro, OR (US)

(72) Inventors: Joel Gillard, Portland, OR (US); Mariah Knight, Hillsboro, OR (US)

(73) Assignee: Acute Innovations LLC, Hillsboro, OR (US)

(*) Notice: Subject to any disclaimer, the term of this patent is extended or adjusted under 35 U.S.C. 154(b) by 379 days.

(21) Appl. No.: 13/942,459

(22) Filed: Jul. 15, 2013

(65) Prior Publication Data

US 2013/0310879 A1  Nov. 21, 2013

Related U.S. Application Data

(63) Continuation of application No. 12/249,252, filed on Oct. 10, 2008, now Pat. No. 8,486,114.

(51) Int. Cl.
| | |
|---|---|
| *A61B 17/56* | (2006.01) |
| *A61B 17/58* | (2006.01) |
| *A61B 17/82* | (2006.01) |
| *A61F 2/30* | (2006.01) |
| *A61B 17/88* | (2006.01) |
| *A61B 17/80* | (2006.01) |
| *A61B 17/00* | (2006.01) |

(52) U.S. Cl.
CPC .............. *A61B 17/823* (2013.01); *A61B 17/809* (2013.01); *A61B 17/8076* (2013.01); *A61B 17/8869* (2013.01); *A61B 2017/00004* (2013.01); *A61B 2017/0088* (2013.01); *A61B 2017/00831* (2013.01); *A61B 2017/00933* (2013.01)

(58) Field of Classification Search
CPC ............... A61B 17/823; A61B 17/809; A61B 17/8869; A61B 2017/00831; A61B 2017/0088; A61B 2017/00004; A61B 2017/00933
See application file for complete search history.

(56) References Cited

U.S. PATENT DOCUMENTS

| 76,141 A | 3/1868 | Barnum |
|---|---|---|
| 190,641 A | 5/1877 | Stouffer |

(Continued)

FOREIGN PATENT DOCUMENTS

| EP | 1080693 A1 | 3/2001 |
|---|---|---|
| EP | 2367489 A | 9/2011 |

(Continued)

OTHER PUBLICATIONS

The Patent Office, U.K. Patent Application No. GB 0010629.4, Patents Act 1977 Search Report under Section 17; search date: Nov. 1, 2000; 1 page.

(Continued)

*Primary Examiner* — Christopher Beccia
*Assistant Examiner* — Diana S Jones
(74) *Attorney, Agent, or Firm* — Kolisch Hartwell, P.C.

(57) ABSTRACT

Method of stabilizing a sternum with a fastening member defining a plurality of cleats. In the method, the fastening member may be disposed on a sternum having a discontinuity, with the fastening member spanning the discontinuity and the cleats contacting the sternum. The fastening member may be arranged with a wire or cable such that the wire or cable extends twice through the fastening member and forms a loop around a portion of the sternum. The fastening member may be crimped to secure both ends of the loop to the fastening member.

20 Claims, 7 Drawing Sheets

(56) References Cited

U.S. PATENT DOCUMENTS

| | | |
|---|---|---|
| 866,144 A | 9/1907 | Kobert |
| 2,171,524 A | 9/1939 | Gates |
| 2,276,571 A | 3/1942 | Grypma |
| 2,452,098 A | 10/1948 | Brooks |
| 2,464,432 A | 3/1949 | Brickman |
| 2,903,772 A | 9/1959 | McKinlay |
| 2,986,787 A | 6/1961 | Ackermann |
| 3,641,629 A | 2/1972 | Beardsley |
| 3,754,303 A | 8/1973 | Pollock |
| 4,050,464 A | 9/1977 | Hall |
| 4,269,180 A | 5/1981 | Dall et al. |
| 4,473,925 A | 10/1984 | Jansen |
| 4,527,308 A | 7/1985 | Tritton et al. |
| 4,587,963 A | 5/1986 | Leibinger et al. |
| 4,643,178 A | 2/1987 | Nastari et al. |
| 4,688,560 A | 8/1987 | Schultz |
| 4,790,303 A | 12/1988 | Steffee |
| 4,896,668 A | 1/1990 | Popoff et al. |
| 5,051,543 A | 9/1991 | McGuire |
| 5,057,113 A | 10/1991 | Mingozzi |
| 5,116,340 A | 5/1992 | Songer et al. |
| 5,190,545 A | 3/1993 | Corsi et al. |
| 5,312,410 A | 5/1994 | Miller et al. |
| 5,318,566 A | 6/1994 | Miller |
| 5,356,412 A | 10/1994 | Golds et al. |
| 5,415,658 A | 5/1995 | Kilpela et al. |
| 5,476,465 A | 12/1995 | Preissman |
| 5,545,168 A | 8/1996 | Burke |
| 5,609,596 A | 3/1997 | Pepper |
| 5,649,927 A | 7/1997 | Kilpela et al. |
| 5,653,711 A | 8/1997 | Hayano et al. |
| 5,665,088 A | 9/1997 | Gil et al. |
| 5,693,046 A | 12/1997 | Songer et al. |
| 5,702,399 A | 12/1997 | Kilpela et al. |
| 5,704,936 A | 1/1998 | Mazel |
| 5,720,747 A | 2/1998 | Burke |
| 5,741,259 A | 4/1998 | Chan |
| 5,741,260 A | 4/1998 | Songer et al. |
| 5,810,824 A * | 9/1998 | Chan .................. A61B 17/842 606/103 |
| 5,810,825 A | 9/1998 | Huebner |
| 5,902,305 A | 5/1999 | Beger et al. |
| 5,935,133 A | 8/1999 | Wagner et al. |
| 5,941,881 A | 8/1999 | Barnes |
| 5,993,449 A | 11/1999 | Schläpfer et al. |
| 5,993,452 A | 11/1999 | Vanderwalle |
| 6,017,345 A | 1/2000 | Richelsoph |
| 6,017,347 A | 1/2000 | Huebner et al. |
| 6,066,141 A | 5/2000 | Dall et al. |
| 6,120,505 A | 9/2000 | Huebner |
| 6,146,386 A | 11/2000 | Blackman et al. |
| 6,381,816 B1 | 5/2002 | Lai et al. |
| 6,616,667 B1 | 9/2003 | Steiger et al. |
| 7,229,444 B2 | 6/2007 | Boyd |
| 7,255,701 B2 | 8/2007 | Allen et al. |
| 8,486,114 B2 | 7/2013 | Gillard et al. |
| 2001/0010110 A1 | 8/2001 | Matsushima et al. |
| 2003/0079315 A1 | 5/2003 | Malin |
| 2005/0124996 A1 | 6/2005 | Hearn |
| 2005/0137608 A1 | 6/2005 | Hearn et al. |
| 2005/0240191 A1 * | 10/2005 | Albertson .......... A61B 17/8076 606/75 |
| 2005/0240198 A1 | 10/2005 | Albertson et al. |
| 2006/0058795 A1 | 3/2006 | Boyd |
| 2006/0276804 A1 | 12/2006 | Molz, IV et al. |
| 2007/0260248 A1 | 11/2007 | Tipirneni |
| 2008/0058815 A1 | 3/2008 | Young |
| 2010/0094294 A1 | 4/2010 | Gillard et al. |
| 2010/0133491 A1 | 6/2010 | Lipke |
| 2010/0319605 A1 | 12/2010 | Petrenko |

FOREIGN PATENT DOCUMENTS

| | | |
|---|---|---|
| GB | 1205346 A | 9/1970 |
| GB | 2351672 B | 7/2001 |
| GB | 2476630 B | 1/2013 |
| JP | 59-39870 U | 3/1984 |
| JP | 1-124664 U | 8/1989 |
| JP | 2000-320730 A | 11/2000 |
| WO | 2010042946 A1 | 4/2010 |

OTHER PUBLICATIONS

Synthes® (USA), Modular Sternal Cable System brochure (2004); 15 pages.

Stryker Orthopaedics, Hip Systems—Dall-Miles Recon & Trauma Cable System product overview internet pages <http://www.stryker.com/jointreplacements/sites/dallmiles/overview.php>, printed Nov. 26, 2006; 8 pages.

Young, Lee W., Authorized officer, International Searching Authority, International Search Report, International Application No. PCT/US2009/60519; search completion date: Dec. 1, 2009; mailing date: Dec. 14, 2009; 2 pages.

Young, Lee W., Authorized officer, International Searching Authority, Written Opinion of the International Searching Authority, International Application No. PCT/US2009/60519; opinion completion date: Dec. 1, 2009; mailing date: Dec. 14, 2009; 7 pages.

U.K. Intellectual Property Office, Patents Act 1977—Examination Report under Section 18 (3), U.K. Patent Application Serial No. GB1107532.2 (counterpart); report date: Apr. 11, 2012; 4 pages.

PRWeb, "Pioneer Surgical Technology, Inc. Announces First Clinical Use of Tritium Sternal Cable Plating System", PRWeb ebooks press release, Jan. 22, 2013; 2 pages.

European Patent Office, "Supplementary European Search Report" in connection with related European Application No. EP 09 82 0047, dated Apr. 17, 2013, 3 pages.

European Patent Office, "European Search Opinion" in connection with related European Application No. EP 09 82 0047, dated Apr. 17, 2013, 4 pages.

European Patent Office, "Examination Report" in connection with related European Application No. EP 09 820 047, dated Jan. 2, 2014, 6 pages.

Codman & Shurtleff, Inc., Sof'Wire Cable System brochure, undated; 6 pages.

* cited by examiner

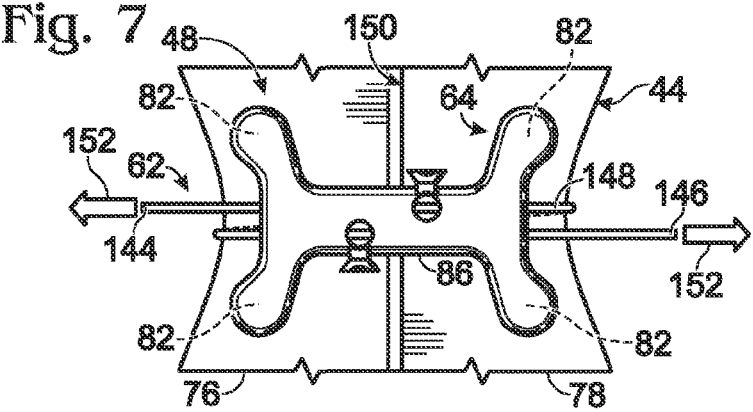
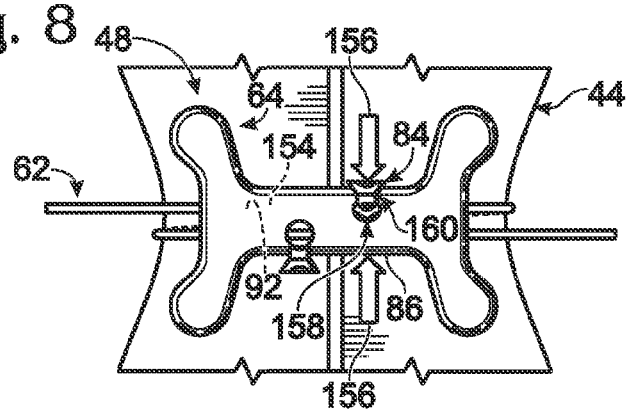
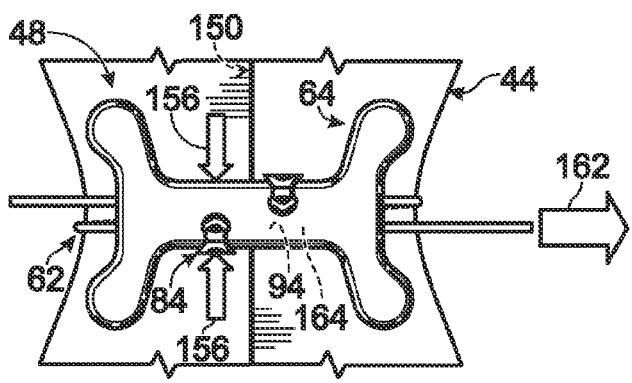
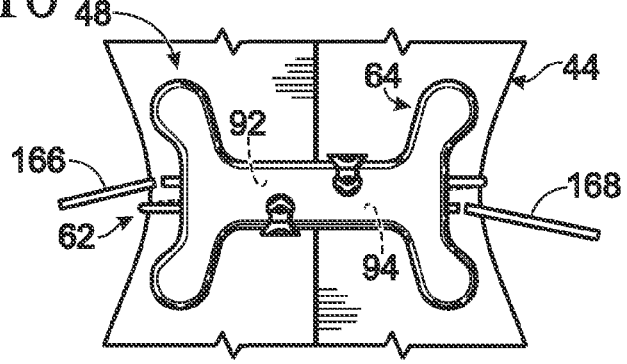

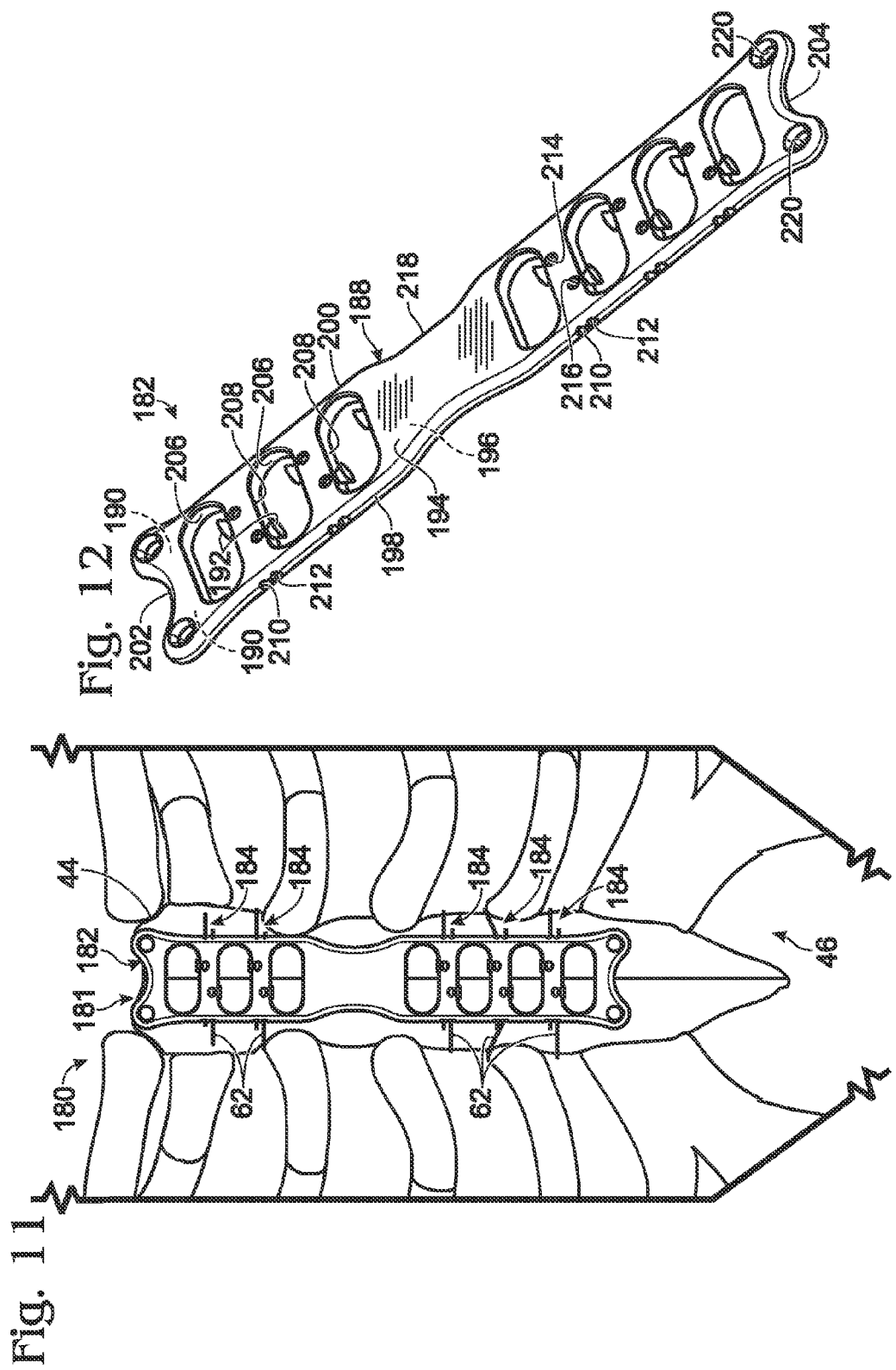

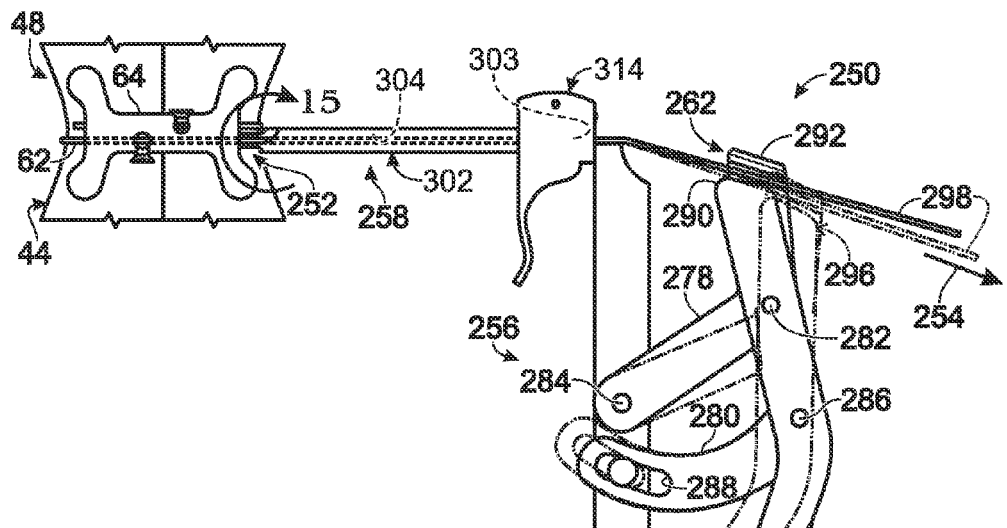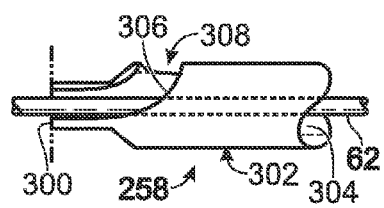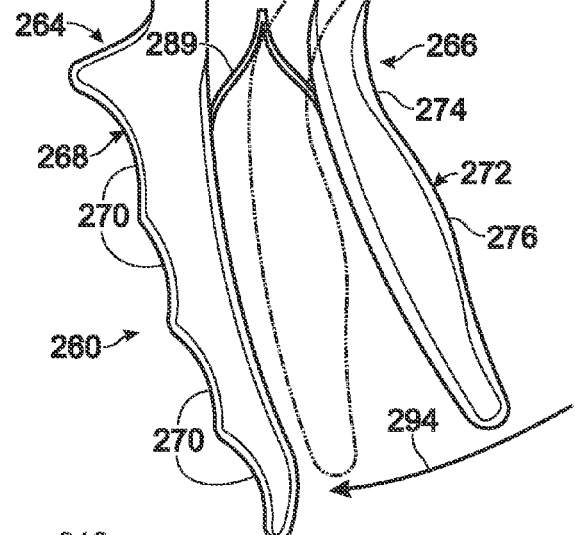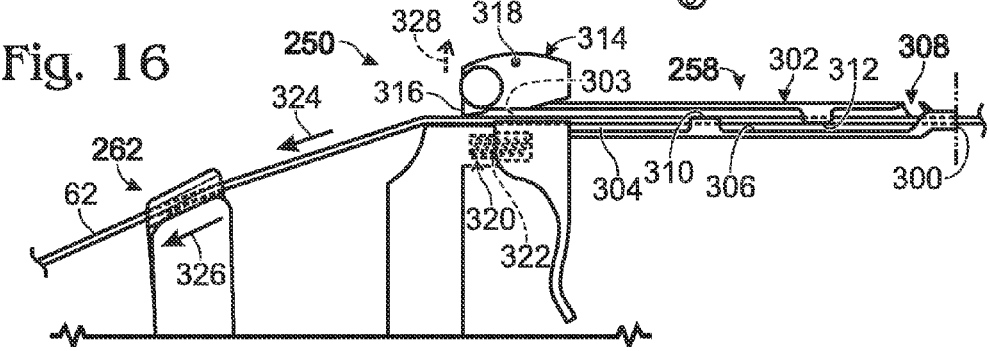

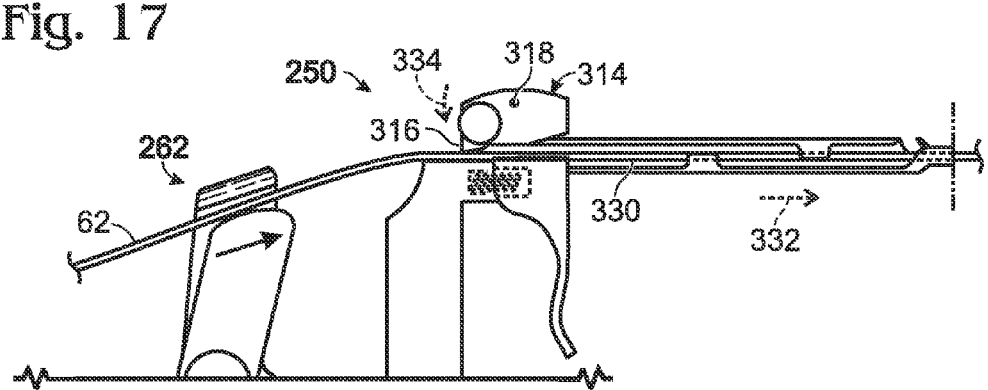
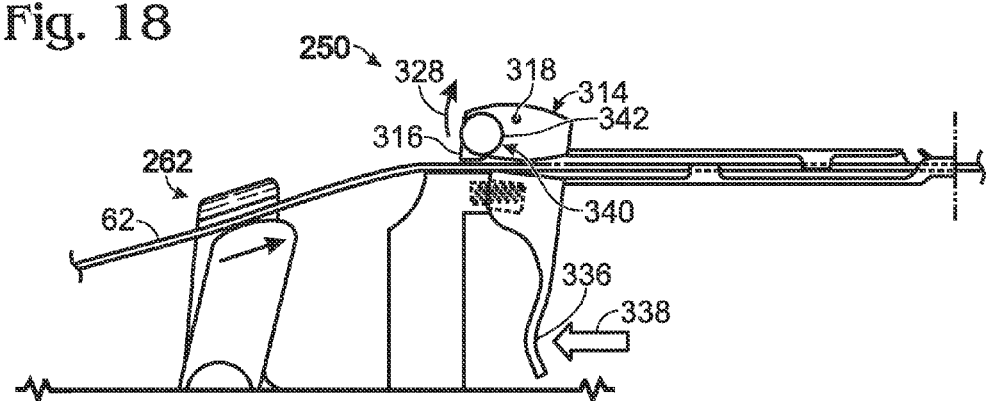

CERCLAGE SYSTEM FOR BONE

CROSS-REFERENCE TO PRIORITY APPLICATION

This application is a continuation of U.S. patent application Ser. No. 12/249,252, filed Oct. 10, 2008, now U.S. Pat. No. 8,486,114, which is incorporated herein by reference in its entirety for all purposes.

INTRODUCTION

The rib cage, or thoracic cage, is composed of bone and cartilage that surround the chest cavity and organs therein, such as the heart and the lungs. In humans, the rib cage typically consists of 24 ribs, twelve thoracic vertebrae, the sternum (or breastbone), and the costal cartilages. The ribs articulate with the thoracic vertebrae posteriorly and, with the exception of the bottom two pairs of ribs (the floating ribs), are connected to the sternum anteriorly using the costal cartilages.

Major surgery inside the chest cavity, such as open heart surgery, requires that the rib cage be opened. The most common procedure for opening the rib cage is for a surgeon to cut the sternum longitudinally, from the sternal notch at the top to the xiphoid process at the bottom. Cutting the sternum creates left and right sternal halves, which form a door to the chest cavity. The surgeon then opens the door by urging the sternal halves apart from one another. After surgery in the chest cavity, the sternal halves are returned to their original positions and secured to one another.

The surgeon may secure the sternum using a cerclage procedure in which wires or cables encircle the sternum at positions along the sternum. Each wire or cable may be locked in a closed loop using a locking device. A commonly used locking device is structured as a sleeve defining a pair of bores for receiving opposing sections of a wire or cable. After the wire or cable sections are disposed in the bores and the wire or cable is properly positioned and tensioned, the sleeve may be deformed, which crimps the wire or cable, to lock the wire or cable to the sleeve. However, with existing cerclage devices, it may be difficult for the surgeon to tension the wire or cable a desired amount, and then lock the wire or cable in place, particularly without the need for assistance and without changing the tension on the wire or cable. If not properly tensioned, the locked wire or cable may slip on the sternum surface if not tight enough, or may bite excessively into the sternum if too tight, in each case compromising bone fixation. Therefore, improved cerclage systems are needed for use on the sternum and/or other bones.

SUMMARY

The present disclosure provides a method of stabilizing a sternum with a fastening member defining a plurality of cleats. In the method, the fastening member may be disposed on a sternum having a discontinuity, with the fastening member spanning the discontinuity and the cleats contacting the sternum. The fastening member may be arranged with a wire or cable such that the wire or cable extends twice through the fastening member and forms a loop around a portion of the sternum. The fastening member may be crimped to secure both ends of the loop to the fastening member.

BRIEF DESCRIPTION OF THE DRAWINGS

FIGS. 6-10 are a series of fragmentary anterior views of a sternum, taken during performance of an exemplary method of fixing a sternum with the cerclage system of FIG. 1, in accordance with aspects of the present disclosure.

FIG. 11 is an anterior view of a bisected sternum fixed with another exemplary cerclage system that holds the rib cage closed after open chest surgery, with the cerclage system utilizing a bone plate and a plurality of wire loops locked to the bone plate along the sternum, in accordance with aspects of the present disclosure.

FIG. 12 is a view of the bone plate of FIG. 11, taken toward an outer surface of the bone plate from a position above and to the side of the bone plate.

FIG. 14 is a side view of an exemplary tensioner device for the cerclage systems of the present disclosure, with the tensioner device being used to tension a wire that extends around a sternum and through a bone plate, in accordance with aspects of the present disclosure.

FIG. 15 is a fragmentary view of a nose of the tensioner device of FIG. 14, taken generally at the region indicated at "15" in FIG. 14.

FIG. 16 is a fragmentary view of the tensioner device and wire of FIG. 14, taken from the opposing side of the tensioner device as the wire is gripped and pulled by jaws of the tensioner device, in accordance with aspects of the present disclosure.

FIG. 17 is a fragmentary view of the tensioner device of FIG. 14, taken as in FIG. 16 but with a section of the wire held under tension and restricted from slippage by a catch member while the jaws are open, in accordance with aspects of the present disclosure.

FIG. 18 is a fragmentary view of the tensioner device of FIG. 14, taken as in FIG. 17 but with the catch member released from engagement with the wire to permit removal of the wire from the tensioner device, in accordance with aspects of the present disclosure.

DETAILED DESCRIPTION

Figure 1:
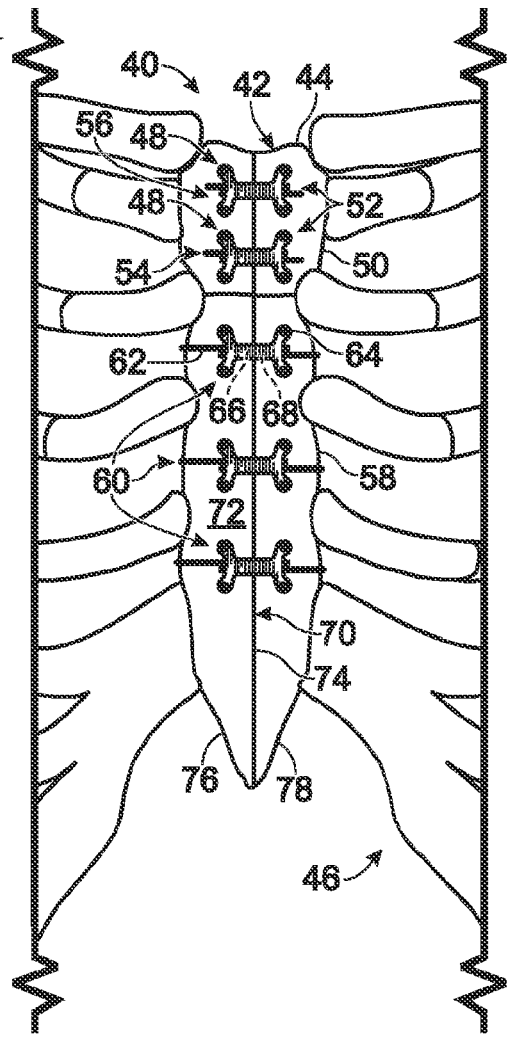
FIG. 1 is an anterior view of a surgically bisected sternum fixed with an exemplary cerclage system that holds a rib cage closed after open chest surgery, in accordance with aspects of the present disclosure.

The present disclosure provides a method of stabilizing a sternum with a fastening member defining a plurality of cleats. In the method, the fastening member may be disposed on a sternum having a discontinuity, with the fastening member spanning the discontinuity and the cleats contacting the sternum. The fastening member may be arranged with a wire or cable such that the wire or cable extends twice through the fastening member and forms a loop around a portion of the sternum. The fastening member may be crimped to secure both ends of the loop to the fastening member.

The present disclosure provides a cerclage device for stabilizing bone. The cerclage device, which may be described as a cerclage assembly, may comprise a bone plate including a plate body and a pair of locking studs. The plate body may form at least one spanning member having opposing end surfaces and defining a pair of channels. Each channel may extend to both opposing end surfaces and may be configured to receive a segment of a wire or cable. The pair of locking studs may project from the spanning member at nonoverlapping positions along the spanning member to permit serial actuation of the locking studs. Each locking stud may be operatively coupled to only one respective channel of the pair such that application of compressive force to the spanning member and locking stud actuates the locking stud, to lock a wire or cable segment to the plate body in the only one respective channel. In some embodiments, the cerclage device may include a plurality of cleats, such as prongs, projecting from the inner surface of the plate body.

The present disclosure also provides another cerclage device for stabilizing bone. The cerclage device comprises a bone plate including a plate body. The plate body may have opposing inner and outer surfaces and a pair of side surfaces that opposingly flank the inner and outer surfaces. The plate body may define a plurality of openings each extending to the inner and outer surfaces to form a plurality of spanning members arranged along the plate body between adjacent pairs of the openings. Each spanning member may define a pair of channels. Each channel may extend along the spanning member to each side surface of the plate body and may be configured to receive a segment of a wire or cable.

The present disclosure also provides a method of fixing a sternum using a wire or cable and a bone plate. The bone plate may include a plurality of cleats, such as prongs, and at least one spanning member defining a pair of channels each extending to both opposing end surfaces of the spanning member. At least a region of a sternum may be encircled with a wire or cable assembled with the bone plate such that segments of the wire or cable are disposed in respective channels of the spanning member of the bone plate. The bone plate may be disposed on the sternum with the spanning member spanning a discontinuity in the sternum and with one or more cleats of the bone plate in engagement with the sternum on each opposing side of the discontinuity. The wire or cable may be locked to the bone plate in each channel.

The present disclosure also provides a method of fixing a bone using a wire or cable and a bone plate. The bone plate may include a spanning member defining a pair of channels extending to both opposing end surfaces of the spanning member. The bone plate also may include a pair of locking studs projecting from the spanning member. Each locking stud may be operatively coupled to a respective channel such that application of compressive force to the spanning member and locking stud actuates the locking stud to lock a wire or cable segment to the bone plate in the respective channel. At least a region of a bone may be encircled with a wire or cable assembled with the bone plate such that segments of the wire or cable are disposed in respective channels of the spanning member. The bone plate may be disposed on the bone with the spanning member spanning a discontinuity in the bone. The locking studs may be actuated serially to lock segments of the wire or cable to the bone plate in the channels at different times.

The cerclage system of the present disclosure may provide substantial advantages over other orthopedic cerclage systems. The advantages may, for example, include any combination of (1) easier and/or faster installation of cerclage devices by one person, (2) independent locking of opposing end segments of a wire or cable in a cerclage device, (3) better control over wire or cable tension in cerclage fixation, and (4) more distributed application of force to bone on opposing sides of a bone discontinuity, resulting in less damage to bone.

Further aspects of the present disclosure are presented in the following sections: (I) an exemplary cerclage system, (II) exemplary methods of stabilizing bone by cerclage, (III) cerclage system with bone plate having multiple spanning members, (IV) plate bodies, (V) cleats, (VI) locking studs, (VII) composition of cerclage system components, (VIII) an exemplary tensioner, and (IX) kits.

I. Exemplary Cerclage System

FIG. 1 shows selected aspects of an exemplary cerclage system 40 stabilizing a bone 42, namely, a bisected sternum 44 of a rib cage 46 after open chest surgery. Cerclage system 40 may utilize one or more cerclage devices 48 (also termed cerclage assemblies) that each encircle at least a region of bone 42. For example, in the present illustration, manubrium 50 of the sternum is secured with an upper pair 52 of discrete cerclage devices 48, which extend only partially around and then through the sternum, indicated at 54. Accordingly, each of these upper cerclage devices 48 encircles only an anterior region 56 of the sternum. In contrast, in the present illustration, body 58 of the sternum is secured with a lower trio 60 of cerclage devices 48, which encircle the sternum completely at three discrete sites along the sternum. Cerclage device 48 may incorporate a wire/cable 62 (hereinafter termed "wire 62" or "the wire") and a bone plate 64.

The terms wire and cable in orthopedic applications generally denote respective single- and multi-stranded structures. Wires and cables thus may have distinct uses and properties (e.g., distinct flexibilities and tendencies to kink and fray). However, throughout the present disclosure, a cable may be substituted for a wire, and vice versa, in a cerclage system, device, or method. The wire or cable may have a smooth surface or may include notches arrayed along at least a portion of the wire/cable, which may facilitate locking the wire/cable to the bone plate. The wire or cable may have any suitable cross-sectional shape including circular, oval, polygonal (e.g., rectangular), or any combination thereof, among others.

Wire 62 may encircle at least a region of bone 42 by extending through bone plate 64, at least partially around and/or through bone 42, and then back through bone plate 64. Opposing segments 66, 68 of wire 62 may lock to bone plate 64 inside the bone plate to hold the cerclage device in position on bone.

Bone plate 64 may span a discontinuity 70 in bone 42. For example, in the present illustration, bone plate 64 is disposed on an anterior surface region 72 of sternum 44. The bone plate spans a cut 74 in the sternum by extending across areas of left and right sternal pieces 76, 78, which are formed by the cut.

FIGS. 2-5 show various views of bone plate 64 in a pre-installation configuration in the absence of wire 62. The bone plate may include a plate body 80, which may (or may not) constitute at least most (or all) of the volume of the bone plate. The bone plate also may include a plurality of cleats, such as prongs 82, and/or a pair of locking studs 84 each projecting from the plate body.

Plate body 80 may include a spanning member 86 configured to span a discontinuity in bone. The spanning member may be central to the plate body. The spanning member may be elongate, with opposing end surfaces 88, 90, and may define a pair of channels 92, 94, which may be bores, extending at least substantially in parallel to each of the opposing end surfaces. Accordingly, channels 92, 94 may be described as horizontal channels because the channels may extend at least substantially horizontally when the bone plate is resting on a horizontal surface, with opposing outer and inner surfaces 96, 98 of the plate generally parallel to the horizontal surface. Channels 92, 94 may be sized to receive segments of a wire in a slidable relationship.

Figure 2:
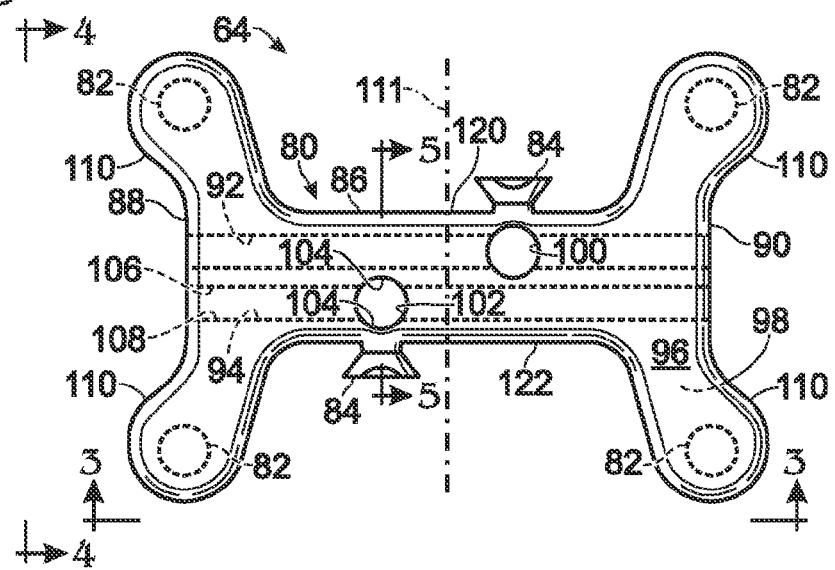
FIG. 2 is a top view of an exemplary bone plate used in the cerclage system of FIG. 1.

Spanning member 86 also may define at least one aperture 100, 102 formed in outer surface 96 of the plate body and intersecting at least one of channels 92, 94 (see FIG. 2). For example, in the present illustration, each of apertures 100, 102, which may be termed vertical apertures, is formed as a through-hole extending to both outer surface 96 and inner surface 98 of the plate body. In other embodiments, each aperture 100, 102 may be formed as a recess in outer surface 96 that does not extend completely through the plate body to inner surface 98. In any event, each channel 92, 94 may overlap a respective aperture 100, 102, to form at least one recess 104 in the channel, which may widen a region of the channel horizontally. Recess 104 may provide a receiver for a kinked region of a wire or cable disposed in the channel.

Recess 104 may be formed in one or both opposing side walls 106, 108 of each channel, to widen the channel on only one side (generally, the side closer to the other channel) or on both opposing sides of the channel. If widened on both sides, each aperture 100, 102 generally has a larger diameter than its corresponding channel, and the aperture may (or may not) be positioned with the central axis of the aperture intersecting the central axis of the corresponding channel. Alternatively, if widened on only one side, the aperture generally is positioned with the central axis of the aperture offset from the central axis of the corresponding channel, toward the other channel, which may permit the aperture to be the same diameter or of smaller diameter than the corresponding channel.

Figure 3:
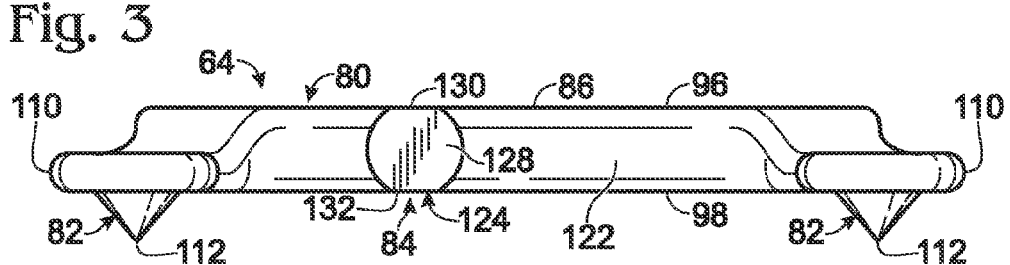
FIG. 3 is a side view of the bone plate of FIG. 2, taken generally along line 3-3 of FIG. 2.
Figure 4:
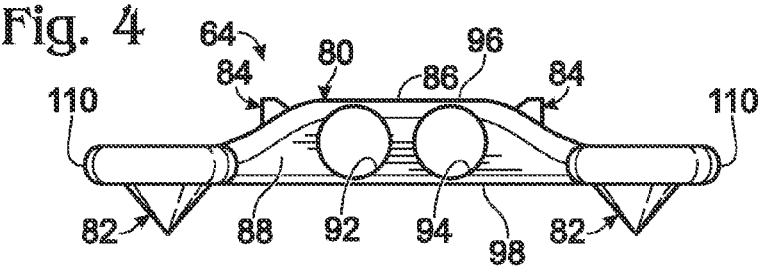
FIG. 4 is an end view of the bone plate of FIG. 2, taken generally along line 4-4 of FIG. 2.
Figure 5:
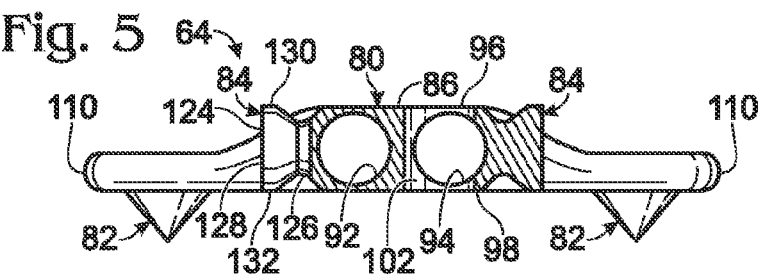
FIG. 5 is a sectional view of the bone plate of FIG. 2, taken generally along line 5-5 of FIG. 2.

The spanning member may (or may not) widen toward one or both opposing end surfaces. For example, plate body 80 may form a plurality of tabs 110 extending from the spanning member near one or both opposing end surfaces 88, 90 of spanning member 86. Tab 110 may be described as a lobe and/or an arm. At least one tab may project from the spanning member adjacent each opposing end surface of the spanning member. For example, in the present illustration, a pair of tabs projects laterally and opposingly from the spanning member adjacent each of the member's opposing end surfaces. A tab (or pair of tabs) may project at least substantially orthogonally or non-orthogonally from a long axis defined by the spanning member. For example, if projecting non-orthogonally, a tab (or pair of tabs) adjacent an end surface of the spanning member may extend generally towards an orthogonal plane 111 bisecting the spanning member, or generally away from the transverse plane (as shown in FIG. 2). Tab 110 may be at least about the same thickness as spanning member 86 or may be substantially thinner (or thicker) than the tab. For example, FIGS. 3-5 shows tabs 110 that are substantially thinner than the spanning member, which reduces the profile of the bone plate above bone to minimize soft tissue irritation.

Further aspects of plate bodies that may be suitable, including aspects of spanning members, channels, apertures, and tabs, are described elsewhere in the present disclosure, such as in Sections III and IV, among others.

Prongs 82 may project from inner surface 98 of plate body 80 (see FIG. 3), such as from tabs 110. For example, at least one prong 82 may project from each tab 110, or one or more (or all) of the tabs may be prong-less. Prong 82 may, for example, have a conical shape that forms pointed tip 112, as shown in FIGS. 3-5. Furthermore, plate body 80 may define a footprint on bone, and tip 112 may engage bone at a position substantially inside and spaced from the footprint's perimeter. Further aspects of prongs that may be suitable are described below in Section V and elsewhere in the present disclosure.

Locking studs 84 may project from plate body 80 and particularly spanning member 86, such as projecting from at least one of opposing side surfaces 120, 122 of the spanning member (see FIG. 2). (Opposing side surfaces 120, 122 connect outer surface 96 and inner surface 98 of the plate body.) Each locking stud may be operatively coupled to a respective channel 92, 94. In other words, the stud is positioned and configured such that application of a suitable force on the locking stud actuates the locking stud to lock a wire/cable to the plate body in the channel. Application of the suitable force on the locking stud may move at least a portion of the locking stud closer to the channel and/or may alter the shape of the channel and/or recess 104, such as by deformation of a channel wall. Each stud 84 may be aligned with a respective aperture 100, 102, with a central axis of the stud intersecting the aperture, such as intersecting a central axis defined by the aperture. Each stud also or alternatively may be aligned with a corresponding channel 92, 94, with a central axis of the stud intersecting the channel, such as intersecting a central axis defined by the channel.

The locking studs may have any suitable positions along the spanning member. The locking studs may be disposed on (project from) the same side surface or may be disposed on (project from) respective opposing side surfaces 120, 122 of the spanning member. Alternatively, or in addition, the locking studs may have distinct positions along the spanning member, meaning that the locking studs are disposed at respective distinct distances, relative to each other, from each opposing end of the spanning member. In some embodiments, the locking studs may be offset sufficiently along the spanning member such that the locking studs are disposed at nonoverlapping positions along the spanning member, as shown in FIG. 2. Locking studs at nonoverlapping positions permit application of an actuating force independently to each locking stud.

Each locking stud 84 may be structured to be pressed toward the spanning member. For example, locking stud 84 may form a head 124 and a neck 126, with the neck disposed between the head and the spanning member (see FIG. 5). Head 124 may taper toward the spanning member and may define an at least substantially planar end surface 128 for receiving a pressing force from a tool, such as a clamp (e.g., pliers), among others. In some embodiments, locking stud 84 may be substantially circular in transverse cross section. Alternatively, or in addition, the locking stud may be sized and positioned not to project substantially above outer surface 96 and/or substantially below inner surface 98 of the plate body. For example, in the present illustration, locking stud 84 has upper and lower facets 130, 132 that are flush with respective outer and inner surfaces 96, 98 of the plate body (see FIGS. 3 and 5). Further aspects of locking studs are described elsewhere in the present disclosure, such as in Section VI, and in U.S. Pat. No. 6,017,347 to Huebner et al., issued Jan. 25, 2000, which is incorporated herein by reference.

II. Exemplary Methods of Stabilizing Bone by Cerclage

The present disclosure provides methods of stabilizing bone by cerclage. A cerclage method may include any suitable combination and order of the steps presented in this section and elsewhere in the present disclosure.

FIGS. 6-10 show a series of fragmentary anterior views of sternum 44 taken during performance of an exemplary method of fixing the sternum with cerclage device 48 (see FIGS. 1-5). The following description of exemplary methods periodically refers to FIGS. 6-10 for illustration.

At least one bone may be selected for stabilization. The bone may be any suitable bone of a human or other vertebrate species. Exemplary bones that may be suitable include at least one bone of the arms (humerus, radius, and/or ulna), wrists (carpal), hands (metacarpal and/or phalange), legs (femur, tibia, and/or fibula), feet (talus, calcaneus, tarsal, metatarsal, and/or phalange), ribs, spine, pelvis, or cranium, or a sternum, clavicle, mandible, or scapula, among others. The bone selected may have a discontinuity (e.g., a fracture, a cut, a nonunion, or the like) or may be otherwise structurally compromised (e.g., osteoporotic bone).

One or more cerclage devices may be selected to stabilize the bone. Each cerclage device may have any suitable combination of the features disclosed herein, particularly a wire (or cable) and a bone plate. The selected cerclage device(s) may include one or more bone plates and one or more wires/cables.

The wire/cable and bone plate of the cerclage device may be assembled. Assembly may include forming a closed loop with the wire/cable and the bone plate. To form the closed loop, the wire/cable may be disposed in channels of the bone plate. For example, the opposing ends of the wire/cable may be placed through respective channels of the spanning member from respective opposing ends of the spanning member. Alternatively, one end of the wire/cable may be placed through one of the channels from one end of a spanning member of the bone plate and then the same end of the wire/cable may be placed through the other channel from the other end of the spanning member. In any event, segments of the wire/cable may be disposed in respective channels of the spanning member.

Assembling the cerclage device may include encircling at least a region of a bone with the wire or cable. For example, the wire/cable may extend completely around a perimeter of the bone, or the wire/cable may extend completely around only a region of the bone that is bounded partly by a perimeter of the bone and partly by interior bone. In some embodiments, the wire/cable may be connected to a curved needle that allows a practitioner to drive the wire/cable through the bone, with the wire/cable entering and exiting the bone at spaced positions, typically on the same side of the bone.

The bone plate may be placed on the bone. Placing the bone plate may position a spanning member of the bone plate across a discontinuity in the bone and may position one or more prongs of the bone plate in engagement with the bone on each opposing side of the discontinuity. The bone plate may be placed on the bone (a) before the bone plate is assembled with the wire/cable, (b) with the bone plate partially assembled with the wire/cable (e.g., with the wire/cable extending through only one channel), or (c) by drawing the bone plate into position against bone, after the bone plate is assembled into a closed loop with the wire/cable, by decreasing the size of the closed loop formed by the assembled cerclage device.

Figure 6:
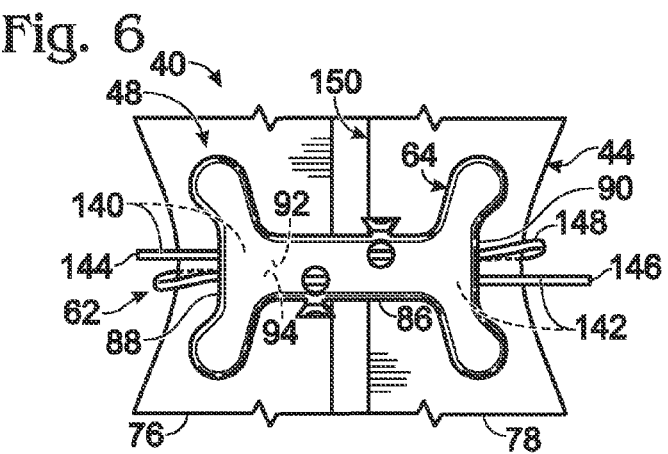

FIG. 6 shows an exemplary configuration of cerclage device 48 produced during a step of assembling the cerclage device around sternum 44, before wire 62 is tensioned and locked. Spaced end regions 140, 142 of the wire may extend in opposing directions through channels 92, 94 and to respective ends 144, 146 of the wire disposed outside the channels. An intermediate region 148 of the wire may extend generally around and/or through sternum 44, from one opposing end surface 88 to other opposing end surface 90 of spanning member 86. Intermediate region 148 may include slack, which may permit a gap 150 to be present in sternum 44 between left and right sternal pieces 76, 78 thereof. In the configuration of FIG. 6, both end regions of the wire may be slidable with respect to the bone plate through respective channels 92, 94. Furthermore, bone plate 64 may be engaged with sternum 44 or, if the loop formed by the cerclage device is large enough, may be spaced from sternum 44.

FIG. 7 shows an exemplary configuration of cerclage device 48 produced by pulling or sliding wire 62, indicated at 152. The step of pulling or sliding may include pulling one or both end regions of the wire such that one or both end regions slide parallel to the channels. Pulling or sliding may be performed by manual engagement of the wire or by engagement with one or more tools that grip end regions of the wire. In any event, the step of pulling or sliding may decrease the size of the closed loop formed by the assembled cerclage device and may decrease the length of intermediate region 148 of the wire. The step of pulling or sliding may reduce the size of gap 150 by tightening the wire against the sternum to draw left and right sternal pieces 76, 78 together. Furthermore, the step of pulling or sliding may dispose bone plate 64 on the sternum, with spanning member 86 spanning gap 150 and with prongs 82 in engagement with the sternum, by drawing the bone plate against the sternum.

The wire/cable may be locked to the bone plate with the wire/cable encircling bone. The step of locking may include a step of locking a respective segment of the wire/cable to the bone plate in each channel of the spanning member. The wire/cable segments may be locked to the bone plate at the same time, for example, if the locking studs are disposed at overlapping positions along the spanning member, such as aligned across the spanning member. Alternatively, the wire/cable segments may be locked to the bone plate at different times, for example, if the locking studs are disposed at non-overlapping positions along the spanning member. If locked at different times, the method may include a step of tensioning the wire/cable after the wire/cable is locked to the bone plate in one channel and before the wire/cable is locked to the bone plate in the other channel. The step of tensioning may be performed with a tensioner tool (e.g., see Section VIII), which may be used to apply tension to the wire/cable with the wire/cable already locked to the bone plate in the other channel. In some embodiments, the wire/cable may be locked to the bone plate in one channel before the wire/cable encircles at least a region of bone.

The wire/cable may be cut at any suitable time. For example, a protruding end segment of the wire/cable may be removed from the wire/cable by cutting, before or after an adjacent segment of the wire/cable is locked in a channel of the bone plate.

FIG. 8 shows an exemplary configuration of cerclage device 48 produced during a step of locking, after wire 62 has been partially tightened around sternum 44. Wire 62 (and particularly wire segment 154) may be locked to bone plate 64 in one of the channels (here, channel 92) by urging locking stud 84 toward channel 92, such as by application of transverse compressive force 156, to spanning member 86 and locking stud 84. The step of locking may be performed, for example, with pliers or any other suitable compression tool. Furthermore, the step of locking may deform wire 62 and/or bone plate 64. For example, the step of locking may crimp wire 62, indicated at 158, and may position the head of locking stud 84 closer to spanning member 86, indicated at 160.

FIG. 9 shows an exemplary configuration of cerclage device 48 produced during a step of locking wire 62 to the bone plate in the other channel (channel 94). Wire 62 may be tensioned further, indicated by tension arrow 162, to further close gap 150, if any, in the sternum. Wire 62 (and particularly wire segment 164) may be locked to bone plate 64 in channel 94 by urging locking stud 84 toward channel 94. The wire may be locked in channel 94 while tension is being applied the wire.

FIG. 10 shows an exemplary configuration of cerclage device 48 fully installed on sternum 44. Wire 62 is locked to the bone plate in both channels 92, 94, both locking studs are depressed, and protruding end segments 166, 168 have been cut from wire 62.

III. Cerclage System with Bone Plate Having Multiple Spanning Members

FIG. 11 shows an anterior view of bisected sternum 44 fixed with another exemplary cerclage system 180 to hold rib cage 46 closed after open chest surgery. Cerclage system may include a cerclage device 181 comprising a bone plate 182 and a plurality of wires 62 in the form of wire loops 184 locked to the bone plate along the sternum.

FIG. 12 shows bone plate 182 taken toward an outer surface of the bone plate from a position above and to the side of the bone plate. Bone plate 182 may include a plate body 188, and prongs 190 and locking studs 192 projecting from the plate body.

Plate body 188 may have opposing outer and inner surfaces 194, 196, which respectively oppose and face/contact bone after the bone plate is installed. Plate body 188 also may have opposing side surfaces 198, 200 and opposing end surfaces 202, 204. Each pair of side surfaces and end surfaces may opposingly flank outer and inner surfaces 194, 196 and may connect outer surface 194 to inner surface 196.

The plate body may have any suitable shape. For example, the plate body may be elongate with generally linear opposing side surfaces and with curved, concave end surfaces. The outer and inner surfaces of the plate body may be substantially planar or may be nonplanar, such as contoured to provide a better fit to a curved surface of the sternum.

The plate body may define a plurality of openings 206. Each opening 206 may be formed in outer surface 194 and may extend to inner surface 196 to create a through-hole.

Openings 206 may be arranged along the plate body to form a plurality of spanning members 208 between adjacent pairs of the openings. Each spanning member 208 may have any of the features and characteristics disclosed above for spanning member 86 (see Section I). For example, each spanning member 208 may be connected to a pair of locking studs 192. In addition, each spanning member may define a pair of channels 210, 212, with each channel extending to each opposing side surface 198, 200 of the plate body. In addition, each channel 210, 212 may intersect a respective aperture 214, 216. Apertures 214, 216 may correspond to apertures 100, 102 of bone plate 64 (e.g., see FIG. 2).

Openings 206 may be arranged in at least two groups, with a bridge region 218 disposed between the groups. In some embodiments, the bridge region may be disposed over the manubrial joint of the sternum when the bone plate is installed.

Plate body 188 also may define additional openings 220 for provisionally or more permanently attaching bone plate 182 to the sternum (or other bone). Openings 220 may be used to suture the bone plate to bone or may receive fasteners such as bone screws.

Figure 13:
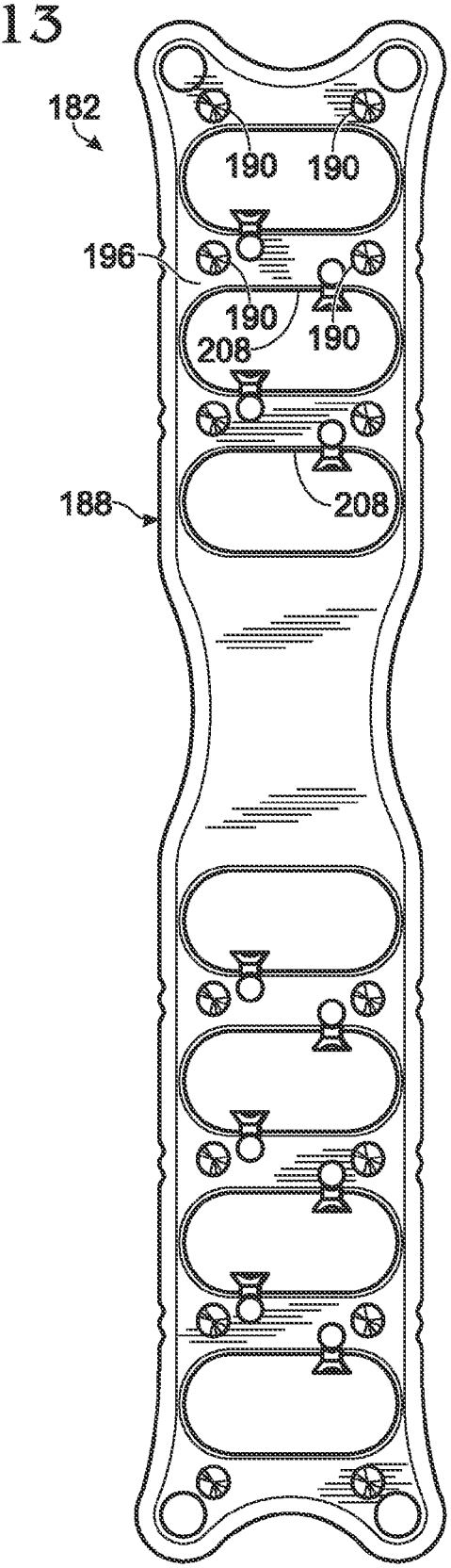
FIG. 13 is a bottom view of the bone plate of FIG. 11, taken toward an inner surface of the bone plate.

FIG. 13 show a bottom view of bone plate 182. The bone plate may incorporate a plurality of prongs 190 that project from inner surface 196 of the plate body. One or more of prongs 190 may project from one or more spanning members 208. For example, in the present illustration, a pair of prongs projects from each spanning member.

IV. Plate Bodies

The bone plates of the present disclosure may include at least one plate body. Each plate body may be constructed to receive at least two segments of at least one wire or cable, with the segments disposed beside each other (side by side).

The plate body may have any suitable construction. For example, the plate body may be of one-piece construction (also termed unitary construction) or may include two or more discrete pieces that are attached to one another, either fixedly or movably. The plate body may be machined, molded, cast, welded, bonded, or any combination thereof, among others.

The plate body may have any suitable shape and dimensions. For example, the plate body may be substantially planar, with an inner surface and/or an outer surface that is at least substantially planar. Accordingly, the plate body (and/or the bone plate) may have a low profile that permits the plate body to be placed under the skin, that is, on bone between the bone and overlying soft tissue. In some embodiments, the outer surface may be less planar than the inner surface, such as to reduce the profile of the plate body where the plate body does not receive a wire or cable segment (e.g., see tabs 110 of bone plate 64 described in Section I). In some embodiments, the inner surface and/or outer surface of the plate body may be constructed (and/or bent peri-operatively) to have a curved shape that corresponds to a curved surface on a target bone. The plate body may have a flat shape, meaning that the body's thickness is much less than the body's width and length, such as at least about 2-, 3-, or 4-fold less, among others. The plate body may have opposing side surfaces and opposing end surfaces that connect the inner and outer surfaces. Each side surface and/or end surface may be linear, curved, or a combination thereof.

The plate body may form any suitable number of spanning members for placement across a bone discontinuity. The spanning member(s) may extend at least substantially parallel, orthogonally, or obliquely to the long axis of the plate body. If the plate body forms a plurality of spanning members, the spanning members may extend at least substantially parallel to one another, or at least one or more of the spanning members may extend obliquely or substantially orthogonally to one or more other of the spanning members. In some embodiments, each spanning member may extend to opposing side surfaces or opposing end surfaces of the plate body or the spanning members may extend to a combination of one more side surfaces and one or more end surfaces of the plate body.

A spanning member may have any suitable shape. The spanning member may be elongate and/or may have a width that is substantially greater than its thickness. The spanning member may have opposing side surfaces that are substantially linear and/or at least substantially parallel to one another. Alternatively, or in addition, the spanning member may have one or more side surfaces that extend at least partially along a curved path. The spanning member generally is thicker than the diameter of a wire or cable to be received by the spanning member and may be wider than twice the diameter of the wire or cable.

A spanning member may define any suitable number of horizontal channels that extend to opposing end surfaces or to opposing side surfaces of the spanning member. For example, the spanning member may define none, 1, 2, 3, 4, or more horizontal channels. If the spanning member defines two or more horizontal channels, a pair (or more) of the channels may extend at least substantially parallel to each other.

A channel may have any suitable shape. The channel may be linear or nonlinear (e.g., extending along an at least partially curved path). The channel may have a circular or non-circular cross-section. A cross section of the channel may be at least substantially uniform along the channel or may vary in shape or size. For example, the channel may taper toward one of its opposing ends, which may cause a wire or cable placed in the channel to travel more easily in one of two opposing directions in the channel. In some embodiments, the channel may be configured to be end-loaded only. To restrict side loading, the channel may define a central axis and may be bounded by side walls that completely surround the central axis along at least a portion of the length of the channel. In some embodiments, the channel may be open along its entire length, to permit side loading of a wire or cable into the channel, such as from the top or bottom the plate body. The term "side loading," means that the wire or cable can be loaded at a position of the wire or cable intermediate its opposing ends.

The plate body may define any suitable number and type of openings, besides the channels, for receiving fasteners, such as bone screws, pins, K-wires, or the like. Each opening may be a through-hole that extends to both the inner and outer surfaces of the plate body. The opening may be circular or may be elongate (i.e., a slot). Furthermore, the opening may be locking (e.g., with an internal thread) or may be nonlocking for a threaded fastener received in the opening.

V. Cleats

The bone plates of the present disclosure may include one or more cleats. A cleat, as used herein, is any fixed projection that projects from the underside of a plate body and that is configured to engage bone when the bone plate is placed on bone, to reduce slippage of the bone plate on the bone. Each cleat may be integral with the plate body, such that the plate body and cleat are formed as one piece, or may be a discrete piece fixed to the plate body.

A cleat may have any suitable shape. The cleat may be conical, frustoconical, cylindrical, spherical, paraboloidal, or the like. The cleat thus may have any suitable cross-sectional shape, such as circular, elliptical, polygonal, or the like. In some examples, the cleat may taper away from the plate body to form a prong having a pointed or bladed tip. Furthermore, the cleat may have a length, measured along the cleat's central axis orthogonal to a plane defined by the inner surface of the bone plate, that is less than, greater than, or about the same as the width of the cleat measured where the cleat meets the plate body. A longer and/or narrower cleat may be suitable to provide better penetration of bone and/or less slippage on bone. On the other hand, a shorter and/or wider cleat may be suitable to minimize damage to bone while still functioning to restrict slippage of the bone plate on bone.

VI. Locking Studs

The bone plates of the present disclosure may include one or more locking studs. A locking stud, as used herein, is any protuberance from a plate body of a bone plate, where the protuberance is configured to be actuated by applying force to the protuberance, such as by application of transverse compressive force to the protuberance and an adjacent portion of the plate body, to lock a wire or cable segment in the channel. The locking stud may, in some cases, be described as a locking button or a locking knob.

A locking stud may have any suitable shape. For example, the locking stud may flare or taper as the stud extends from the plate body, or the locking stud may have walls that extend orthogonally from the plate body. Accordingly, the locking stud may be cylindrical, frustoconical, conical, spherical, paraboloidal, or the like.

A locking stud may have any suitable position on a plate body. For example, the locking stud may project from a side surface of the plate body or an end surface of the plate body, among others. In some embodiments, the locking stud projects from a spanning member of the bone plate. The spanning member may have only one, only a pair, or three or more locking studs projecting from the spanning member.

A locking stud may have any suitable connection to the plate body. In some embodiments, the plate body and locking stud may be formed collectively as one piece. Alternatively, the locking stud may be a discrete piece from the plate body, which may be attached to the plate body by any suitable mechanism, such as by welding, bonding, a friction fit or press fitting (e.g., into a hole defined by the plate body), a fastener, or any combination thereof, among others.

VII. Composition of Cerclage System Components

The cerclage system of the present disclosure may have components formed of any suitable biocompatible material(s) and/or bioresorbable (bioabsorbable) material(s). Illustrative biocompatible materials that may be suitable for a bone plate, a wire/cable, or a tensioner of the cerclage system include (1) metal (for example, titanium or titanium alloy, cobalt-chrome alloy, stainless steel, etc.); (2) plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramic (for example, alumina, beryllia, calcium phosphate, and/or zirconia, among others); (4) composite (for example, carbon-fiber composites); (5) bioresorbable material or polymer (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); (6) bone material or bone-like material (e.g., bone chips, calcium phosphate crystals (e.g., hydroxyapatite, carbonated apatite, etc.)); or (7) any combination thereof.

The components of a cerclage device may be formed of the same or different materials. For example, the bone plate at least one wire/cable both may be formed of metal, the bone plate and the wire/cable both may be formed of plastic, the bone plate may be formed of metal and the wire/cable may be formed of plastic (or vice versa), and/or the bone plate and/or the wire cable may be formed of a bioresorbable polymer (which may be a bioresorbable plastic).

VIII. Exemplary Tensioner

The present disclosure provides a tensioner, also termed a tensioner device or tensioner tool, to apply tension to a wire or cable. The tensioner may be used with any of the cerclage devices disclosed herein or may be used in any other system in which a wire or cable, and particularly a surgical wire or cable, needs to be tensioned, such as during surgery. The tensioner may provide a cyclical drive with an unlimited drive length, tensioning without coiling the wire or cable as it is pulled, a catch mechanism to selectively restrict reverse travel of a wire or cable under tension, side loading and unloading of a wire or cable, a relatively constant hand position relative to a surgery site, or any combination thereof, among others. Accordingly, relative to the prior art, the tensioner may be (1) easier to load and operate, (2) more accepting of kinked wires or cables, (3) less damaging to a wire or cable, and/or (4) suitable for a broader range of surgical applications.

The present disclosure provides a device for tensioning a surgical wire or cable. The device may include a guide portion that includes a nose defining a longitudinal channel configured to receive a surgical wire or cable and also defining a lateral entryway to the channel that extends continuously along the nose to opposing proximal and distal ends of the channel, to permit side loading of the wire or cable into the nose. The entryway may be nonlinear, such as sinuous, to retain the wire or cable in the nose. For example, the entryway may wrap at least partway around the nose, such as following a twisted path at least to generally opposing sides of the nose, as the entryway extends from the proximal end to the distal end of the nose. The device also may include a drive portion connected to the guide portion and including at least one handle that is pumpable to pull the wire or cable in increments through the channel of the guide portion. The at least one handle thus may reciprocate as the drive portion is operated. In some embodiments, the drive portion may cyclically grip and release the wire or cable as the at least one handle is pumped. The tensioner further may include a catch member pivotably connected to the guide portion and biased toward engagement with the wire or cable such that the catch member engages the wire or cable and keeps a portion of the wire or cable under tension when the drive portion is not gripping the wire or cable.

FIG. 14 shows a side view of an exemplary tensioner 250 loaded with a wire 62 of cerclage device 48 and being used to tension the wire. In the present illustration, the cerclage device is assembled around sternum 44. However, the tensioner may be used to tension a wire or cable being installed on and/or in any other bone(s) and/or being used for any other surgical purpose. The tensioner may be engaged, indicated at 252, with bone plate 64 of cerclage device 48, to apply a counterforce when the wire is under tension. Wire 62 may be pulled away from the engaged bone plate in a direction defined by the tensioner and indicated generally by an arrow at 254. The tensioner may include a drive portion 256 connected to a guide portion 258.

The drive portion may be configured to drive translational motion of wire 62 with respect to guide portion 258 (and bone plate 64). The drive portion may be operated manually, for example, with the drive portion configured to be supported, positioned, and powered by only one hand (or by both hands). The drive portion may utilize a handle portion 260 operatively coupled to jaws 262. The handle portion may be squeezed repeatedly (i.e., pumped) to pull wire 62 incrementally through guide portion 258, through a repeated cycle of (1) closure of the jaws to grip the wire, (2) movement of the closed jaws away from guide portion 258, and (3) opening of the jaws and movement of the open jaws back toward the guide portion.

Drive portion 256 may include pivotably coupled first and second body members 264, 266, which, respectively, may be positioned relatively distally and proximally with respect to a person holding and using the tensioner. First body member 264 may be attached more directly to guide portion 258, such as fixed to the guide portion, and thus may serve to connect the guide portion to second body member 266.

Handle portion 260 may be formed by the first and second body members in a lower portion of each member. First body member 264 may form a distal handle region 268, which may define a set of indentations 270 for receiving the fingers of a user's hand. Similarly, second body member 266 may form a proximal handle region 272, which may define an indentation 274 for receiving the thumb of the user's hand and may include a convex surface region 276 for engagement by the palm of a user's hand.

The first and second body members may be connected by an upper arm 278 and a lower arm 280. The upper and lower arms may be pivotably coupled to the body members to define first, second, and third pivot axes 282-286. Lower arm 280 also may define a slot 288 that guides sliding movement of the lower arm past the first body member. The relative positions of handle regions 268, 272 of the body members also may be biased toward a spaced configuration by a spring 289 (here, a wishbone spring) that urges the handle regions apart.

Jaws 262 of the drive portion may be positioned to receive a wire 62 from guide portion 258. The jaws may be formed by second body member 266 and upper arm 278. In particular, a top region of second body member 266 may form a lower jaw element 290 and a top region of upper arm 278 may form an upper jaw element 292. The upper and lower jaw elements may cooperatively receive and grip the wire at respective upper and lower sides of the wire. In some embodiments, upper jaw element 292 may have the general shape of an inverted U that receives lower jaw element 290. The legs of the inverted U may opposingly flank lower jaw element 290 when the jaws are open, to keep the wire between the jaws.

Drive portion 256, with wire 62 loaded in jaws 262, may be operated as follows. A user may squeeze handle regions 268, 272 toward one another, as indicated by an arrow at 294, to place second body member 266, upper arm 278, and lower arm 280 in the positions indicated by phantom outline in FIG. 14. Before the handle regions are urged together, jaws 262 may be in an open configuration in which wire 62 is not gripped by the jaws. As the handle regions are urged together, second body member 266 may pivot about first pivot axis 282 to close jaws 262 such that the jaws grip the wire. After the jaws are closed, as the handle regions are squeezed together further, second body member 266 and upper arm 278 may collectively pivot about second pivot axis 284, and with respect to first body member 264, to move closed jaws 262 away from guide portion 258 to a more spaced position, which is indicated in phantom outline at 296. Movement (or attempted movement) of the jaws may advance the wire through the guide portion toward the jaws (and/or may increase the tension on the wire). During handle movement, lower arm 280 may pivot about third pivot axis 286 to facilitate sliding of the lower arm past the first body member using slot 288. The user's pressure on the handle portion then may be released (i.e., reduced or removed), which, through the action of spring 289, may open jaws 262 and return the open jaws back to their starting position, to complete a single drive cycle. Overall, as a result of movement of the closed jaws with their gripped wire 62, an end segment 298 of wire 62 disposed proximal to jaws 262 may be lengthened, which may tighten wire 62 around sternum 44 (or another encircled bone or bone region). The handle regions then may be pressed together again and released to repeat the cycle and pull the wire farther. Accordingly, repeatedly squeezing and releasing (i.e., pumping) the handles may allow the jaws to repeatedly grip the wire at successive positions along the wire, which may drive the wire in corresponding increments through the guide portion.

FIGS. 14-16 shows selected aspects of guide portion 258, with FIG. 16 showing an opposing side of the guide portion relative to FIGS. 14 and 15. Guide portion 258 may be configured to define a path along which wire 62 extends from jaws 262 to a distal end 300 of the guide portion. In addition, the guide portion may be configured to permit side loading of a wire into the guide portion while restricting side unloading of the wire from the guide portion until a user is ready to remove the wire. The option of side loading may be a substantial advantage if the wire is long and/or kinked. Alternatively, or in addition, the wire may be end-loaded into the guide portion and/or drive portion.

The guide portion may include a nose 302 defining a longitudinal channel 304 through which the wire extends between a proximal end 303 and distal end 300 of the nose. The nose may be structured as a tube, and may define a lateral entryway 306 for side loading the wire into channel 304.

The lateral entryway may extend continuously from proximal end 303 to distal end 300 along a nonlinear path, to restrict inadvertent separation of the wire from the tube. In particular, when tensioned, the wire may be substantially linear in the guide portion and thus cannot easily assume a nonlinear shape corresponding to the nonlinear path, unless tension is released. Entryway 306 may have a sinuous shape. For example, the entryway may twist, indicated at 308 in FIGS. 15 and 16, by wrapping at least partway around nose 302, such as at least to an opposing side of the nose as the entryway extends from one opposing end to the other opposing end of nose 302. In some embodiments, the entryway may twist near distal end 300 of the nose. In any event, the wire may be placed into the tube by at least partially wrapping the wire around the nose. Alternatively, or in addition, the entryway may bend as it extends along a side of the nose, as shown in FIG. 16. For example, entryway 306 may be defined at least in part by at least one flange, such as generally opposing flanges 310, 312. To summarize, the lateral entryway may be configured such that the wire cannot be removed laterally from the nose without bending the wire.

The tensioner may include a catch member 314 that keeps the wire under tension by selectively restricting reverse travel of the wire relative to forward travel of the wire. In particular, the catch member may maintain tension on the wire by engagement with the wire to preferentially restrict longitudinal slippage of the wire in a direction opposite to the direction the wire is pulled by the tool. The catch mechanism thus may permit the jaws to release their grip on the wire in preparation for another cycle of pulling the wire, while the wire is under tension, without losing the tension due to wire slippage. Accordingly, the catch member may allow the drive portion to perform a plurality of consecutive drive cycles without wire slippage.

FIG. 16 shows selected aspects of catch member 314. The catch member may include a tooth 316, also termed a pawl. Tooth 316 may be positioned proximal to nose 302, generally in line with channel 304, such that the tooth can engage the wire proximal to nose 302. In addition, the catch member may be pivotably coupled to guide portion 258 and/or first body member 264, via a pivot mechanism, such as a pin, defining a pivot axis 318. Pivotal motion of the catch member may provide adjustable engagement of tooth 316 with the wire, permitting the tooth to pivot into greater or lesser (or no) engagement with the wire. Furthermore, the pivotal position of catch member 314 may be biased by a biasing member 320, such as a spring 322. The biasing member may be configured to urge tooth 316 into engagement with the wire, by counterclockwise motion in FIG. 16. As a result, the tooth can selectively restrict travel of the wire through the guide portion in one of two opposing directions.

FIGS. 16-18 show distinct configurations of catch member 314. FIG. 16 presents jaws 262 in a closed configuration and wire 62 being pulled in a forward direction 324 by jaws 262, resulting in coupled motion of the jaws, indicated at 326, and the wire. Motion of the wire urges the catch member in a pivot direction indicated at 328, which results in decreased pressure of the tooth on the wire, thereby permitting tensioning of the wire by wire travel past the tooth in the forward direction, away from distal end 300 of the tensioner. In contrast, FIG. 17 presents jaws 262 in an open configuration. However, a leading section 330 of the wire may be under tension, which urges the wire in a reverse direction 332, toward distal end 300. However, the tension is maintained substantially because reverse travel of the wire urges tooth 316 in pivot direction 334, and into tighter engagement with the wire, with increased pressure on the wire. FIG. 18 shows catch member 314 disposed in a released configuration in which tooth 316 may be out of engagement with the wire. The released configuration may be achieved manually by pressing a lever 336 (e.g., a trigger) of catch member 314, as indicated by a force arrow at 338. Catch member 314 may be locked in the released configuration by a locking mechanism 340, which may be actuated by pivoting the catch member to the released configuration. The locking mechanism may be released manually by operation of a user control, such as a knob 342 that controls the locking mechanism.

IX. Kits

The cerclage system may be provided as a kit. The kit may include any combination of one or more bone plates as disclosed herein, one or more wires and/or cables, a tensioner, a compression tool to actuate a locking stud, a cutting tool to cut wires/cables, a wire/cable puller tool to grip and pull both ends of a wire/cable at the same time, fasteners (such as bone screws, pins, K-wires, pegs, etc.), a drill, a guide device for guiding the drill and/or fastener placement, a saw for cutting bone, and instructions for use, among others. The bones plates may include a set of bone plates of different size and/or shape for use on different bones, on different regions of the same bone, and/or on different sizes of the same bone. Some or all of the components of each kit may be provided in a sterile condition, such as packaged in a sterile container.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of stabilizing a sternum with a fastening member defining a plurality of cleats, the method comprising:
   arranging the fastening member with a wire or cable such that the wire or cable extends twice through the fastening member and forms a loop around at least a portion of the sternum; and
   crimping the fastening member to produce tight engagement between the fastening member and the wire or cable, such that both ends of the loop are secured to the fastening member;
   wherein the crimped fastening member spans a discontinuity of the sternum and contacts the sternum with the plurality of cleats.

2. The method of claim 1, wherein the discontinuity forms a pair of sternal segments, and wherein at least one of the cleats of the crimped fastening member is in contact with each of the sternal segments.

3. The method of claim 2, wherein a different pair of the cleats of the crimped fastening member is in contact with each of the sternal segments.

4. The method of claim 1, wherein the steps of arranging and crimping are each performed twice such that a pair of loops are secured to the fastening member.

5. The method of claim 4, wherein the pair of loops are provided by a first wire or cable and a second wire or cable.

6. The method of claim 4, wherein the pair of loops are spaced from each other along the sternum.

7. The method of claim 4, wherein the steps of arranging and crimping are each performed at least three times such that at least three loops are secured to the fastening member.

8. The method of claim 1, wherein the fastening member includes a plate body having an inner surface region that faces the sternum after the step of crimping, and wherein the cleats taper away from the inner surface region to form prongs.

9. The method of claim 1, wherein the step of crimping secures both ends of the loop to the fastening member at the same time.

10. The method of claim 1, wherein the fastening member has a plurality of tabs from which the cleats project.

11. The method of claim 1, further comprising a step of tensioning the wire or cable with a tool before the step of crimping.

12. The method of claim 11, wherein the tool holds the wire or cable in a tensioned configuration while the fastening member is crimped.

13. The method of claim 1, further comprising a step of cutting through the wire or cable after the step of crimping.

14. The method of claim 13, wherein the step of cutting through the wire or cable cuts the loop.

15. The method of claim 1, wherein a spanning member of the fastening member spans the discontinuity, and wherein the spanning member and the cleats are formed collectively as one piece.

16. The method of claim 1, wherein the steps of arranging and crimping are performed with a plurality of fastening members and a plurality of wires or cables to form a plurality of loops arranged along the sternum from one another.

17. The method of claim 1, wherein the wire or cable extends through the fastening member parallel to an axis, and wherein the step of crimping includes a step of applying compressive force to the fastening member orthogonal to the axis.

18. The method of claim 17, wherein the step of applying compressive force includes a step of contacting a projection of the fastening member with a compression tool.

19. The method of claim 18, wherein the step of contacting a projection includes a step of contacting a pair of projections of the fastening member with a compression tool.

20. The method of claim 1, further comprising a step of sectioning the sternum longitudinally to create a pair of sternal segments before the step of disposing.

* * * * *